US00PP25417P3

(12) United States Plant Patent
Hammett

(10) Patent No.: US PP25,417 P3
(45) Date of Patent: Apr. 7, 2015

(54) ***DAHLIA* PLANT NAMED 'MYSTIC FANTASY'**

(50) Latin Name: *Dahlia variabilis*
Varietal Denomination: Mystic Fantasy

(71) Applicant: Keith Hammett, Auckland (NZ)

(72) Inventor: Keith Hammett, Auckland (NZ)

( * ) Notice: Subject to any disclaimer, the term of this patent is extended or adjusted under 35 U.S.C. 154(b) by 135 days.

(21) Appl. No.: 13/986,663

(22) Filed: May 22, 2013

(65) Prior Publication Data

US 2013/0326781 P1 Dec. 5, 2013

Related U.S. Application Data

(60) Provisional application No. 61/689,260, filed on May 31, 2012.

(51) Int. Cl.
*A01H 5/00* (2006.01)

(52) U.S. Cl.
USPC ..... Plt./321

(58) Field of Classification Search
USPC ..... Plt./321
See application file for complete search history.

*Primary Examiner* — Annette Para
(74) *Attorney, Agent, or Firm* — James M. Weatherly; Cochran Freund & Young LLC

(57) ABSTRACT

A new cultivar of *Dahlia* plant named 'Mystic Fantasy' that is distinguishable by a compact rounded habit, glossy mahogany-black divided leaves and flamingo pink single flowers with a soft yellow halo, raspberry eye and dark central disc.

3 Drawing Sheets

Figure 1:
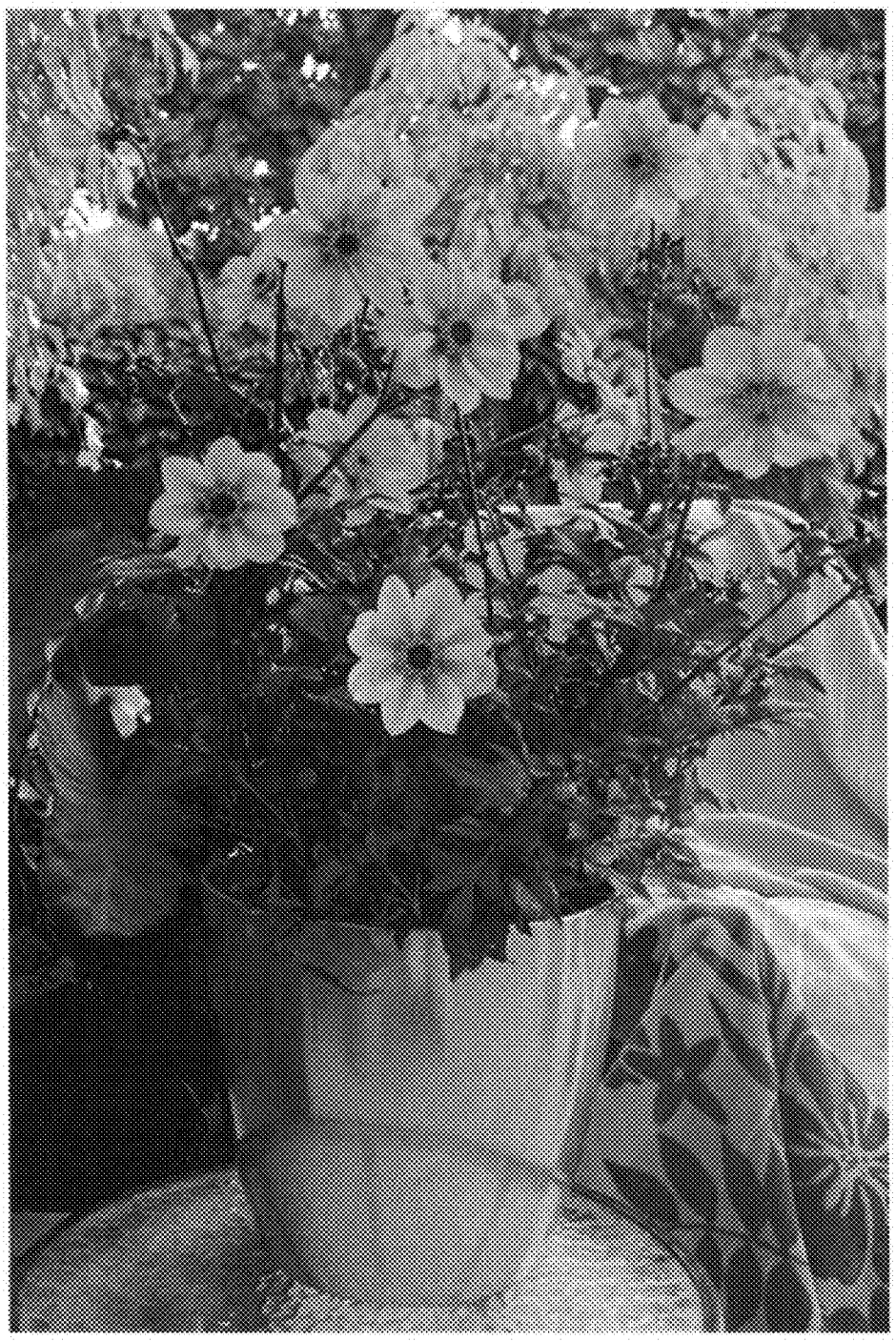

Genus and species: *Dahlia variabilis.*
Variety denomination: 'Mystic Fantasy'.

BACKGROUND OF THE NEW PLANT

The present invention relates to a new and distinct cultivar of *dahlia* grown for use in mixed combinations, beds and the landscape. The new invention is known botanically as *Dahlia variabilis* and will be referred to hereinafter by the cultivar name 'Mystic Fantasy'. This application is co-pending with the application for the inventor's variety of *Dahlia* plant named 'Mystic Memories'.

The specific epithet *variabilis* represents a hybrid seedling line that came from crossing various original wild species in the early 1800's, and refers to the species' wide range of flower color and shapes. *Dahlia* is in the family Compositae. The flower of 'Mystic Fantasy' is a "single" form blossom and exhibits a single row of ray flowers surrounding a central cluster of disk florets.

'Mystic Fantasy' was selected as a seedling that resulted from the controlled cross-pollination carried out by the inventor in a cultivated area of Auckland, New Zealand in 2007. The inventor selected as female parent an individual plant of the inventor's variety *Dahlia variabilis* 'Fifteen Love' (unpatented). The chosen male parent was the inventor's variety *Dahlia variabilis* 'Knockout' (U.S. Plant Pat. No. 18,339). Seed was collected from the female parent and sown with the intention of making a selection from the seedlings that resulted.

'Mystic Fantasy' was selected in 2008 based on the criteria of leaf color, leaf shape, plant height, self supporting plants, single blooms and flower color. Selection was conducted by the inventor, in Auckland, New Zealand. The unique traits that distinguish the new *Dahlia* variety named 'Mystic Fantasy' from other varieties of *Dahlia* known to the inventor are glossy mahogany-black divided leaves and flamingo pink single flowers with a soft yellow halo, raspberry eye and dark central disc.

The first asexual reproduction of 'Mystic Fantasy' was conducted in 2008 in Auckland, New Zealand. The method of asexual propagation utilized was softwood cuttings taken from the one year old tuber of the original selected seedling. Since that time under careful observation, the distinguishing characteristics have been determined stable, uniform, and to be reproduced true to type in subsequent generations of asexual propagation.

SUMMARY

The following traits have been repeatedly observed and represent the distinguishing characteristics of the new *Dahlia* cultivar named 'Mystic Fantasy'. These traits in combination distinguish 'Mystic Fantasy' from all other existing varieties of *Dahlia* known to the inventor. 'Mystic Fantasy' has not been tested under all possible conditions and phenotypic differences may be observed with variations in environmental, climatic, and cultural conditions, however, without any variance in genotype.

1. 'Mystic Fantasy' exhibits a compact rounded habit.
2. The foliage of 'Mystic Fantasy' is glossy mahogany black in color.
3. 'Mystic Fantasy' bears flamingo pink flowers with a soft yellow halo, raspberry eye and dark central disc.
4. The flowers of 'Mystic Fantasy' are single.
5. After one year of growth, plants of 'Mystic Fantasy' are 60.0 cm in height and 30.0 cm in width.
6. At maturity, plants of 'Mystic Fantasy' are 80.0 cm in height and 60.0 cm in width.
7. 'Mystic Fantasy' prefers a rich moist well-drained medium.
8. 'Mystic Fantasy' is hardy in USDA Zones 9 and higher.

COMPARISON WITH PARENTAL LINES AND KNOWN VARIETY

The new *Dahlia* named 'Mystic Fantasy' is distinguishable from the parents predominantly by flower and foliage color. The flowers of 'Fifteen Love' are of collarette form (that is, bearing a collar of petaloids stamens around the disc) and uniformly orange-red in color. The flowers of 'Knockout' are single and uniformly yellow in color.

The variety of *Dahlia* which is considered by the inventor to most closely resemble 'Mystic Fantasy' is *Dahlia* 'Mystic Memories' (U.S. Plant Patent Application pending). The flowers of 'Mystic Fantasy' are flamingo pink with a soft yellow halo, raspberry eye and dark central disc, while the flowers of 'Mystic Memories' are soft peach with orange-red highlights.

BRIEF DECRIPTION OF THE DRAWINGS

Figure 2:
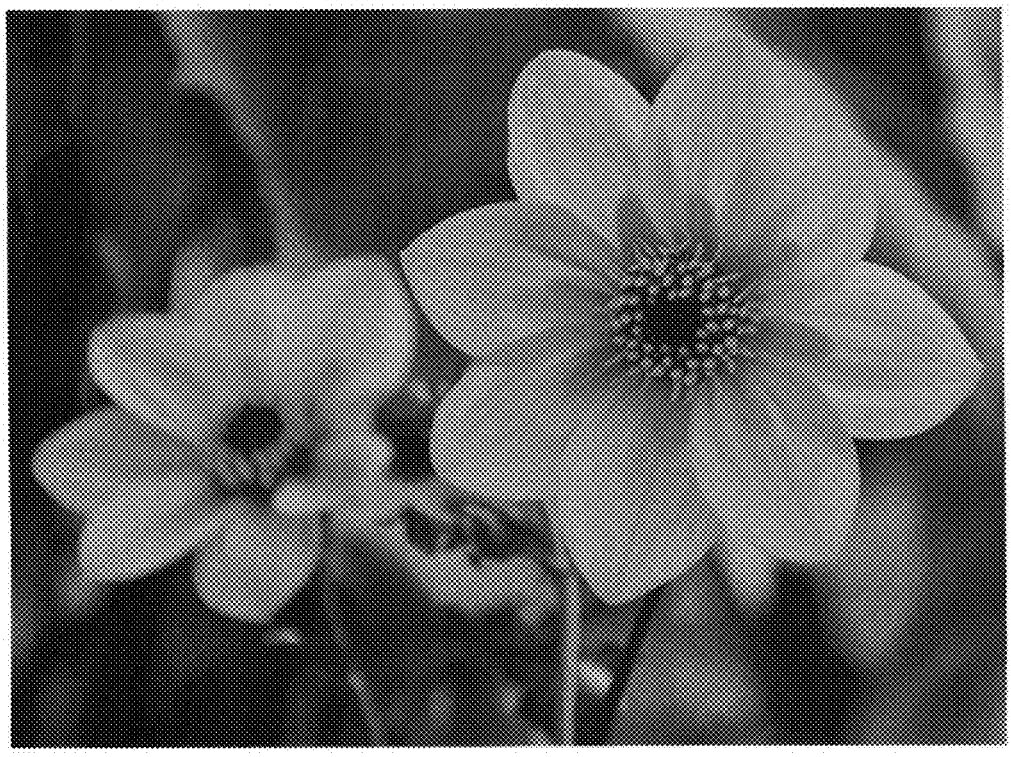
Figure 3:
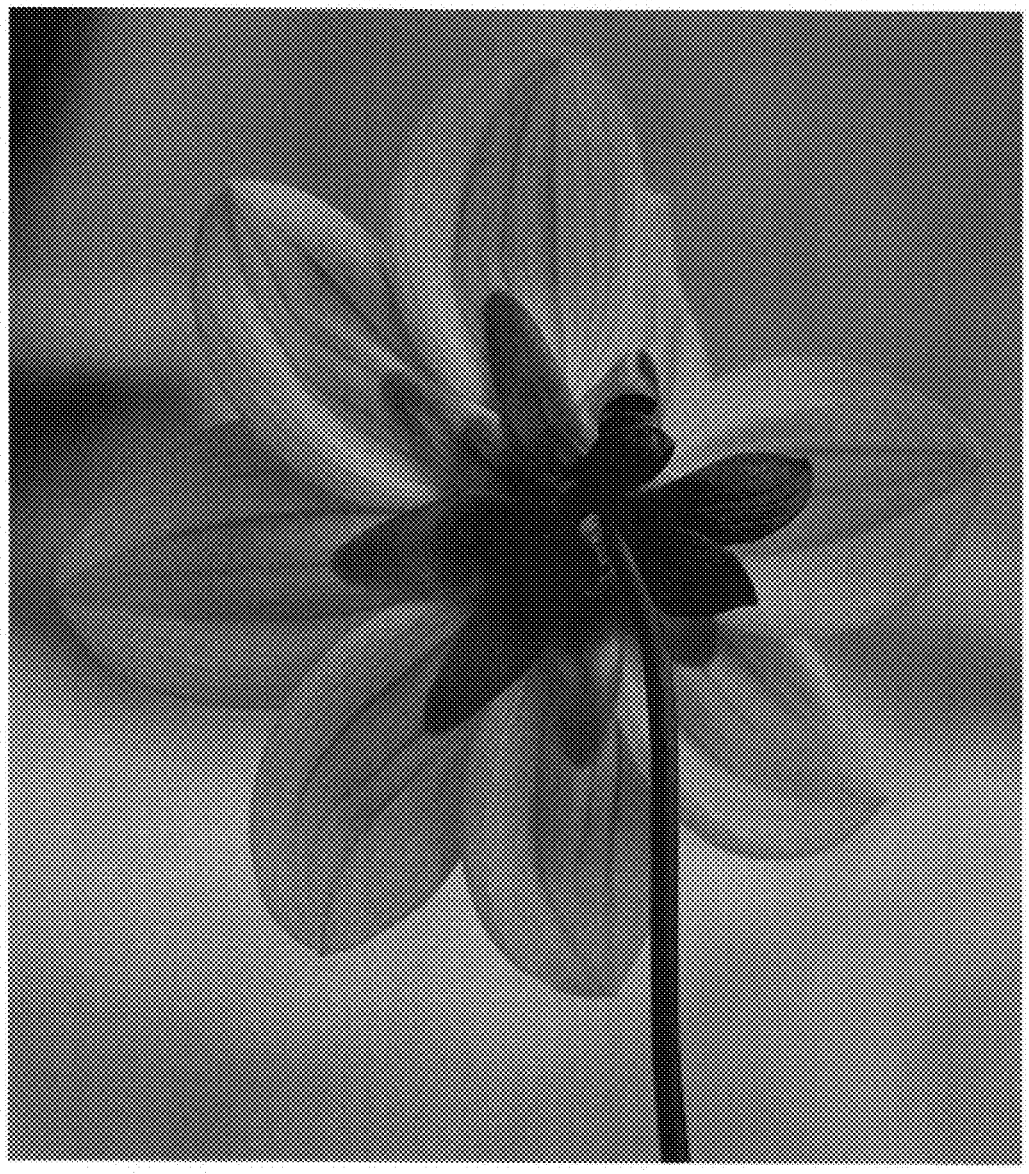

The accompanying color drawings labeled FIG. 1, FIG. 2 and FIG. 3 illustrate the overall appearance of the new *Dahlia* cultivar named 'Mystic Fantasy' showing the colors as true as is reasonably possible to obtain in colored reproductions of this type. Colors in the photographs may differ from the color values cited in the detailed botanical description, which accurately describes the actual colors of the new *Dahlia* variety named 'Mystic Fantasy'. The photographs were made from digital photographs of four months old from a cutting plant grown outdoors in Santa Barbara, Calif.

The drawing labeled FIG. 1 depicts the entire plant in bloom and demonstrates that the foliage of 'Mystic Fantasy' is consistently mahogany-black when grown in full sun. Any part of the plant which is in shade, including the shade of other plant parts, turns to olive green in color. This coloration is reversible such that the olive-green foliage returns to mahogany-black when exposed or re-exposed to full sun.

The drawing labeled FIG. 2 depicts a close-up view of the face of a flower of 'Mystic Fantasy' showing the flamingo red petals and dark central disc.

The drawing labeled FIG. 3 depicts a close-up view of the reverse of a flower of 'Mystic Fantasy' showing the dark translucent phyllaries and parallel pink-red veins.

The drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Dahlia* cultivar named 'Mystic Fantasy'. Observations, measurements, values and comparisons were collected in Santa Barbara, Calif. from a 12-month-old plant grown in the landscape. Color determinations were made in accordance with The 2007 Royal Horticultural Society Colour Chart from London, England, except where general color terms of ordinary dictionary significance are used. Growing requirements are similar to the species.

Botanical classification:

*Family*.—Compositae.
*Genus*.—*Dahlia*.
*Species*.—*variabilis*.
*Denomination*.—'Mystic Fantasy'.
*Common name*.—*Dahlia*.
*Parentage*.—*Dahlia variabilis* 'Mystic Fantasy' is a seedling that resulted from the controlled cross-pollination of the following parents: Female parent: *Dahlia variabilis* 'Fifteen Love' (unpatented). Male parent: *Dahlia variabilis* 'Knockout' (U.S. Plant Pat. No. 18,339).
*Propagation method*.—Tissue culture and cuttings from virus-indexed mother stock.
*Rooting system*.—Fine and fibrous.
*Vigor*.—Vigorous.
*Habit*.—Upright habit.
*Use*.—For use in mixed combinations, beds and the landscape.
*Type*.—Annual in most regions, perennial in USDA Zone 9 and warmer.
*Dimensions at* 12 *months of age from a cutting*.—60.0 cm in height, 30.0 cm in width.
*Cultural requirements*.—Grow in full sun with regular water, and well-draining potting soil.
*Pest susceptibility*.—Susceptible to aphids.
*Disease susceptibility*.—Susceptible to mildew in highly humid conditions.
*Hardiness*.—USDA Zone 9 and higher.

Stem:

*Color*.—RHS N186C.
*Shape*.—Cylindrical.
*Dimensions*.—50.0 cm in length. Diameter ranges from 1.0 cm at base to 0.5 cm below uppermost leaf.
*Surface*.—Glabrous.
*Internode length* (*average*).—5.0 cm to 12.0 cm.

Foliage:

*Type*.—Evergreen.
*Leaf arrangement*.—Opposite.
*Leaf division*.—Simple.
*Leaf dimensions* (*average*).—15.0 cm to 18.0 cm in length and 12.0 cm to 15.0 cm in width.
*Leaf color* (*adaxial surface*).—Ranges between RHS N186A and RHS 200A.
*Leaf color* (*abaxial surface*).—RHS 138B.
*Margin*.—Ciliate and pinnatisect.
*Leaf shape*.—Hastate.
*Leaf base*.—Attenuate.
*Leaf apex*.—Apiculate.
*Leaf venation pattern*.—Pinnate.
*Vein color*.—Adaxial surface: RHS N186A. Abaxial surfaces: RHS 137A.
*Vein midrib* (*abaxial surface only*).—Lightly pubescent; Hairs, 1.0 mm long, fine, light gray.
*Leaf surfaces* (*abaxial surfaces*).—Slightly puberulent.
*Leaf surfaces* (*adaxial surfaces*).—Glabrous.
*Leaf attachment*.—Petiolate.
*Leaf fragrance*.—None observed.
*Petiole shape*.—Sulcate.
*Petiole dimensions*.—0.5 cm to 2.0 cm in length and 3.0 mm to 4.0 mm in width.
*Petiole color*.—Adaxial surface: RHS N186A. Abaxial surfaces: RHS 152C with streaks of RHS N186A.

Inflorescence:

*Inflorescence type*.—Capitulum, classified as "single" form, with single row of ray flowers surrounding a central cluster of disk florets.
*Aspect*.—Facing upward and outward.
*Inflorescence quantity*.—15 to 20 per 2-liter container plant.
*Dimensions of inflorescence* (*average*).—8.0 cm in diameter and 2.0 cm in depth.
*Inflorescence shape*.—Radiate with center disk.

*Blooming seasons*.—Summer and fall.
*Lastingness of inflorescence*.—8 to 10 days until petal fall.

Peduncle:
*Dimensions* (*average*).—20.0 cm in length and 0.3 cm to 0.4 cm in diameter.
*Shape*.—Cylindrical.
*Surface*.—Glabrous.
*Color*.—RHS N186C.

Bud:
*Shape*.—Oblate.
*Dimensions* (*average*).—1.2 cm in height and 1.5 cm in diameter.
*Surface*.—Glabrous.
*Appearance*.—Semi-glossy.
*Color*.—RHS 153D except RHS 187B at flattened apex immediately prior to opening.
*Apex*.—Obtuse.
*Base*.—Truncate.

Ray florets:
*Petals*.—Quantity per inflorescence: 8. Dimensions (average): 3.25 cm in length and 2.0 cm to 2.2 cm in width. Shape: Obovate. Apex: Obtuse with minute acute tip. Base: Cuneate. Margin: Entire. Surface (adaxial and abaxial): Glabrous. Arrangement: Radiate. Colors (adaxial): Predominantly ranging between RHS 52D and RHS 37D, becoming RHS N34A towards and at base. A yellow halo approximately RHS 9C appears to permeate the petal. Color (abaxial): RHS 49C. Veins (adaxial): Fine, parallel, color RHS 52A. Veins (abaxial): Pronounced, broad, parallel, color RHS 52A.

Disk florets:
*Disc diameter*.—18.0 mm.
*Quantity of disk florets*.—50 to 60 per inflorescence.
*Dimensions*.—1.3 cm in length and 1.5 cm in width.
*Disk color*.—Ranges between RHS 59A and RHS N77A.
*Petals*.—8 in number.
*Petals fused or unfused*.—Fused.
*Petal color*.—RHS 46A becoming burnt in appearance at apex, RHS N77A.
*Petal apex*.—Acute.
*Petal surface* (*ventral and dorsal surfaces*).—Glabrous.

Receptacle:
*Receptacle dimensions*.—0.7 cm in depth and 2.5 cm in diameter.
*Receptacle surface*.—Glabrous.
*Receptacle color*.—RHS 53A.

Phyllaries:
*Inner phyllary*.—Number: 8. Shape: Elongated ovate. Dimensions: 2.0 cm in length and 8.0 mm to 11.0 mm in width. Texture: Scarious, waxy. Color (adaxial and abaxial surfaces): Translucent, colorless except for veins RHS 184A which merge and darken to RHS N187A or darker at base. Apex: Rounded to subacute. Base: Truncate. Margin: Entire. Surface (adaxial and abaxial): Glabrous.
*Outer phyllary*.—Number: 5 in number. Shape: Obovate, reflexed. Dimensions: 1.0 cm to 1.2 cm in length and 0.4 cm to 0.6 cm in width. Color (both surfaces): RHS 202A. Apex: Obtuse. Base: Truncate. Margin: Entire. Surface (both surfaces): Glabrous, glossy, ribbed. Approximately 8 longitudinal ribs 0.5 cm to 0.8 mm apart.

Reproductive organs:
*Stamens*.—5 in number.
*Stamen attachment*.—Filament adnate to ventral surface of corolla.
*Stamen length*.—8.0 mm in length.
*Stamen color*.—RHS 150B.
*Anther*.—Connate.
*Anther color*.—RHS 25A.
*Pollen*.—Present.
*Quantity*.—Large amount.
*Pollen color*.—RHS 24A.
*Pistil*.—One present.
*Pistil length*.—15.0 mm in length.
*Stigma dimensions*.—3.0 mm in length and 0.5 mm in width.
*Stigma form*.—Plumose.
*Stigma color*.—RHS N25A.
*Stigma shape*.—Bifurcate.
*Ovary position*.—Inferior.
*Ovary color*.—RHS N144A.
*Ovary shape*.—Rotund.
*Ovary dimensions*.—2.0 mm in width and 3.0 mm in height.

Seed: None observed to date.

I claim:

1. A new and distinct cultivar of *Dahlia* plant named 'Mystic Fantasy' as described and illustrated herein.

* * * * *